US006852106B2

(12) United States Patent
Watson et al.

(10) Patent No.: US 6,852,106 B2
(45) Date of Patent: Feb. 8, 2005

(54) IMPLANTABLE REFILLABLE AND PORTED CONTROLLED RELEASE DRUG DELIVERY DEVICE

(75) Inventors: David A. Watson, Westwood, MA (US); Robert W. Shimizu, Acton, MA (US); Richard LaPorte, Waltham, MA (US)

(73) Assignee: Control Delivery Systems, Inc., Watertown, MA (US)

( * ) Notice: Subject to any disclaimer, the term of this patent is extended or adjusted under 35 U.S.C. 154(b) by 0 days.

(21) Appl. No.: 10/013,946

(22) Filed: Dec. 13, 2001

(65) Prior Publication Data

US 2002/0138068 A1 Sep. 26, 2002

Related U.S. Application Data

(60) Provisional application No. 60/255,114, filed on Dec. 14, 2000.

(51) Int. Cl.[7] .......................... A61K 9/22; A61M 31/00; A61M 37/00
(52) U.S. Cl. ................. 604/891.1; 604/288.03
(58) Field of Search ....................... 604/288.01, 288.02, 604/288.03, 288.04, 890.1, 891.1

(56) References Cited

U.S. PATENT DOCUMENTS

| 3,640,269 | A | | 2/1972 | Delgado |
| 4,784,646 | A | | 11/1988 | Feingold |
| 5,085,644 | A | * | 2/1992 | Watson et al. .............. 604/153 |
| 5,185,003 | A | | 2/1993 | Brethauer |
| 5,205,820 | A | | 4/1993 | Kriesel |
| 5,647,855 | A | | 7/1997 | Trooskin |
| 5,695,490 | A | * | 12/1997 | Flaherty et al. .......... 604/891.1 |
| 5,836,935 | A | * | 11/1998 | Ashton et al. ........... 604/891.1 |

* cited by examiner

Primary Examiner—Michael J. Hayes
Assistant Examiner—Catherine S. Williams
(74) Attorney, Agent, or Firm—Ropes & Gray LLP (57) ABSTRACT

An implantable, refillable, rate controlled drug delivery device is disclosed that includes a base structure having at least a first opening and a second opening, the base structure defining a chamber, a septum covering the first opening and configured to substantially prevent leakage from the first opening to an exterior of the device, a drug delivery tube comprising a first and second distal end, wherein the first distal end of the tube communicates with the chamber through the second opening, and at least one rate-limiting permeable membrane disposed across a passage between the base structure and the second distal end of the drug delivery tube, which membrane passively regulates drug delivery. The drug delivery device is used to provide controlled drug delivery to an internal portion of the body and is advantageously leak-proof and does not rely on a pressure differential to drive the drug from the device.

20 Claims, 6 Drawing Sheets

IMPLANTABLE REFILLABLE AND PORTED CONTROLLED RELEASE DRUG DELIVERY DEVICE

RELATED APPLICATIONS

This application claims priority from U.S. Patent Provisional Application Ser. No. 60/255,114, filed Dec. 14, 2000, incorporated herein by reference.

TECHNICAL FIELD

The present invention relates to infusion systems implantable in a mammalian body to administer a drug. More particularly, the present invention relates to a subcutaneously implantable direct delivery access port permitting multiple intermittent injections, which may be used in combination with a subcutaneous drug infusion apparatus, such as a catheter, and at least one rate-limiting permeable membrane to regulate drug delivery.

BACKGROUND

To overcome some of the disadvantages of repeated venipuncture injections, implantable infustate injection ports were developed. Such devices provide a bolus or therapeutic dose of the drug contained therein to a particular location within the patient's body. To replenish the drug in the implanted device, a subcutaneous device can be provided in fluid communication with the drug delivery device, such as provided in U.S. Pat. No. 5,137,529, incorporated herein by reference. These implantable devices typically include an internal chamber, a penetrable self-sealing septum, and a hollow male outlet connector, which are subcutaneously implanted within the patient.

The outlet connector is attached to a catheter element or drug delivery tube for transmitting drugs from the internal chamber to a predetermined area of the patient's body, such as a cavity, a large vein, a tumor, or an injury site. Once installed, the internal chamber can be periodically filled with drug by inserting a hypodermic needle through the patient's skin and the septum to permit injection of the drug into the internal chamber. Devices of this general type can be effectively utilized for dispensing drug in the body of a patient over a prolonged period of time since the injection port provides a means for administering additional medicament into the device by means of a syringe inserted into the injection port.

Typically, such devices utilize pumps of one form or another. That is, they are designed to pump the drug from a reservoir through a tube to a site in the body. One of the disadvantages of such systems is that there is a net change in volume in the reservoir and/or the receptor. This net change in volume is undesirable where, for example, a drug is being delivered to an area such as the brain where slight volume changes can cause a large change in intracranial pressure.

Another problem encountered by conventional devices is device leakage. U.S. Pat. No. 4,857,053 to Dalton, for example, discloses that drug delivery ports utilizing elastomeric materials, such as silicon rubber, as the penetrable wall material tend to develop leaks.

Therefore, a need exists for an implantable, refillable, rate controlled leak-proof drug delivery device that does not rely on pressure to drive a drug from the device.

SUMMARY OF THE INVENTION

An advantage of the present invention is an implantable and refillable drug delivery device utilizing a septum that substantially prevents leakage.

Another advantage of the present invention is an implantable and refillable drug delivery device utilizing at least one rate-limiting permeable membrane that passively regulates drug delivery.

According to the present invention, the foregoing and other advantages are achieved in part by an implantable, refillable, rate controlled drug delivery device. The device includes a base structure having at least a first opening and a second opening, the base structure defining a chamber; a septum covering the first opening and configured to substantially prevent leakage from the first opening to an exterior of the device; a drug delivery tube communicating with the chamber through the second opening, and at least one rate-limiting permeable membrane disposed within said drug delivery tube, which membrane passively regulates drug delivery.

In accordance with the present invention, the foregoing and other advantages are also achieved in part by a method of controlling the delivery of a drug to an internal portion of a body by administering a drug to an internal portion of the body through the device according to the present invention to control the delivery of the drug.

Additional advantages of the present invention will become readily apparent to those skilled in the art from the following detailed description, wherein embodiments of the invention are described simply by way of illustrating of the best mode contemplated in carrying

DESCRIPTION OF THE INVENTION

Figure 1:
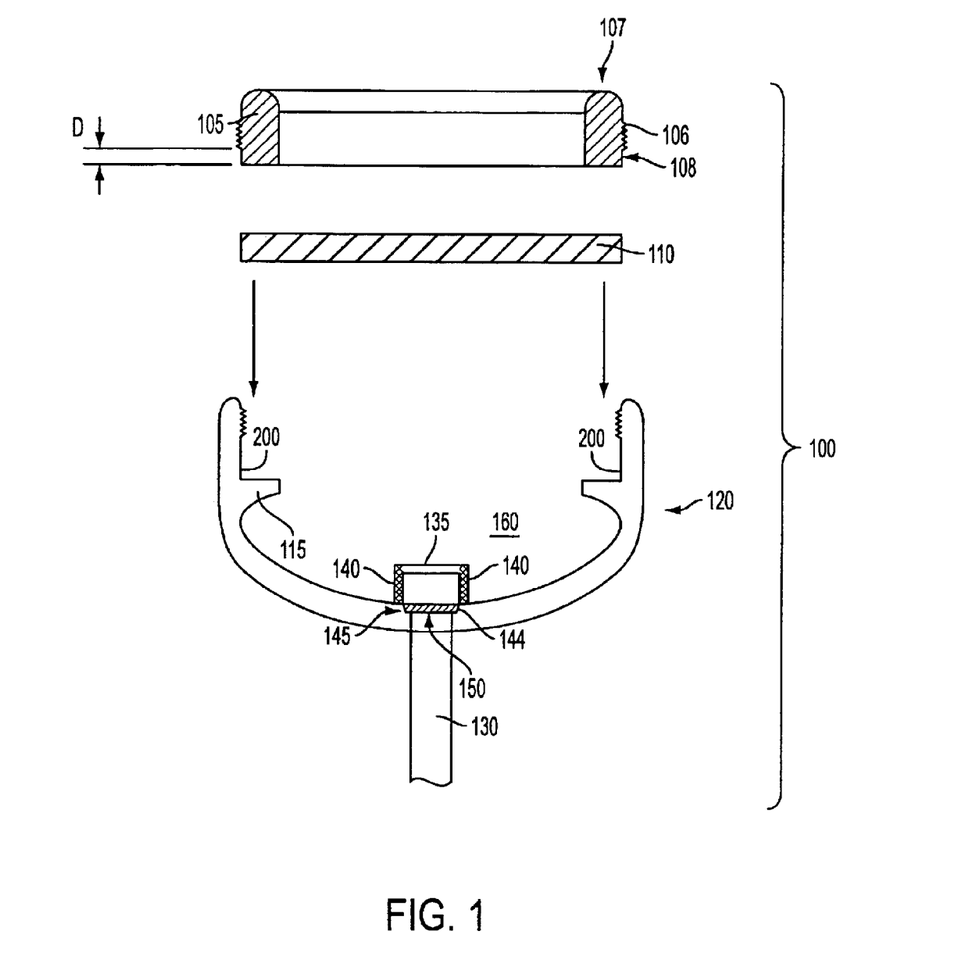
FIG. 1 shows a cross-sectional view of a device in accordance with the present invention.

As shown in the appended figures, the present invention provides an implantable, refillable, rate controlled drug delivery device, generally designated in the respective figures by the reference number 100. FIG. 1 shows device 100 comprising an elastomeric perforatable septum 110, a lower base structure 120, a catheter or drug delivery tube 130, a retaining ring 105 provided to retain septum 110 in place, and rate-limiting permeable membrane 150 disposed across an opening 145 in the lower base structure in communication with drug delivery tube 130.

The perforatable septum 110 defines, in conjunction with the lower base structure 120, a chamber or reservoir 160 in which a drug may be stored. Optionally, a filter housing 135 having one or more filter elements 140 may be provided between the reservoir 160 and the rate-limiting permeable membrane 150. An upper portion of the filter housing 135 may comprise a needle stop. A needle stop presents a barrier to passage of the needle and prevents the needle from passing through the upper portion to the rate-limiting permeable membrane 150 where it could contact and damage the rate-limiting permeable membrane. To protect the filter elements 140, the filter elements may be disposed beneath the housing 135 or may be disposed substantially perpendicular to the septum 110 so that a needle pushed perpendicularly through the septum to contact the inner wall of the base structure 120 would not contact the filter elements 140. Alternatively, filter elements 140 may be arranged in a tapered configuration extending from the needle stop portion of the filter housing 135. The filter housing 135 itself may take many forms, such as, but not limited to, a substantially rectangular or hemispherical structure. Alternatively, the filter housing 135 may simply comprise a needle stop, such as a perforated plate having a plurality of perforations of a diameter smaller than the smallest expected needle diameter. This needle stop would permit insertion and securement of a simple hemispherical filter element about the rate-limiting permeable membrane.

Drug delivery tube 130 is attached, by conventional means such as, but not limited to, an interference fit, adhesive connection, or microferrule connection to lower base structure opening 145. This drug delivery tube 130 may itself be a catheter or may comprise a connector, known to those skilled in the art, for a catheter or another form of drug delivery tube. The drug delivery tube may take many conventional forms. As shown, one of these forms includes a tube 130 having a central passage and a closed end 137. Perforations 138 through the wall at one or more desired sites provide for fluid communication between the central passage and the outside of the tube at the sites.

Opening 145 may be provided at other locations within reservoir 160 and may advantageously be located in a side wall thereof to facilitate placement in other orientations and locations within a patient. In this regard, it is noted that the shape of lower base structure 120 in FIG. 1 is only one representative structure and is non-limiting. For example, the base structure may be specifically configured for placement in various areas of the body and may also include tabbed portions on an exterior thereof to facilitate securement of the base structure to, for example, bones or tissue. The outer surface of the lower base structure 120 could, for example, have a substantially planar bottom, a convex bottom, or a concave bottom. The inner bottom surface of lower base portion 120 does not have to correspond to the outer surface of the lower base structure, but may so correspond to minimize weight and cost. As shown in FIG. 1, the inner bottom surface of lower base portion 120 is gently curved between the opening 145 and the septum ledge 115. This curvature helps prevent stagnation of fluid within the reservoir 160.

Figure 6A:
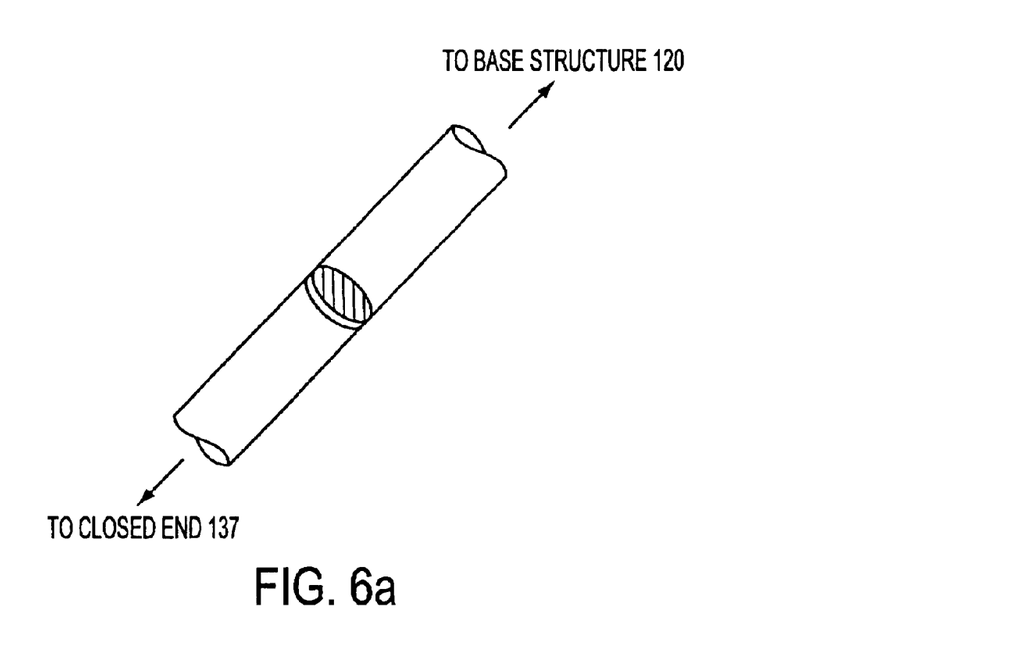
FIGS. 6a and 6b show non-limiting configurations of the rate-limiting permeable membrane in accord with the invention.
Figure 6B:
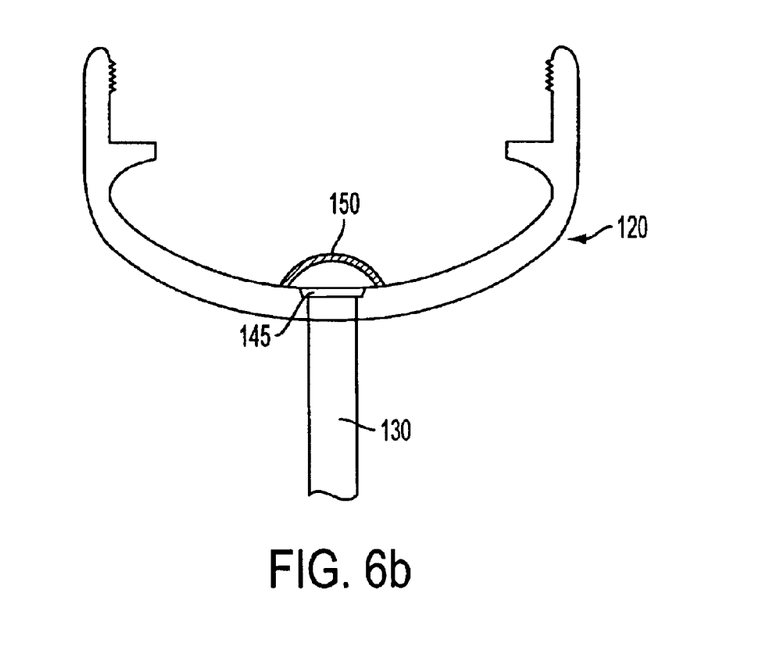

Although the rate-limiting permeable membrane 150 is shown in FIG. 1 as occupying a position across opening 145, the rate-limiting permeable membrane may be disposed in any position so long as it is permitted to control the rate of drug delivery to the target area of drug delivery by diffusion. Namely, the rate-limiting permeable membrane 150 is disposed across a passage between the base structure 120 and a distal end of drug delivery tube 130 such that the rate-limiting permeable membrane 150 passively regulates drug delivery. The passage, as referred to herein, is a simply a fluid path between the reservoir 160 of the base structure and an outlet for the dispensed drug. This outlet may include a distal end of a drug delivery tube 130. The passage is not limited to the physical structure of the opening 145 in the base structure or any appurtenant connections with a drug delivery tube 130, but also includes fluid paths between the reservoir 160 and the opening 145. Thus, rate-limiting permeable membrane 150 may be, for example, disposed within drug delivery tube 130, as shown in FIG. 6a, or within chamber 160, as shown in FIG. 6b. Alternatively, more than one rate-limiting permeable membrane 150 may be used. As shown in FIG. 1, a recessed or depressed area 144 is formed adjacent opening 145 to permit at least partial insertion of the rate-limiting permeable membrane 150 therein to provide lateral restraint of the rate-limiting permeable membrane.

The septum 110, base structure 120, retaining ring 105, and drug delivery tube are all made of conventionally medically safe materials. In embodiments of the present invention, base structure 120 and retaining ring 105 are made of titanium or a suitable medically acceptable stainless steel material (e.g., 316L Grade SS). Alternatively, base structure 120 and retaining ring 105 may comprise a relatively hard biocompatible non-metallic substance, such as Udel® Polysulfone made by Amoco Corp, a high density or ultra-high molecular weight polyethylene (HDPE/UHMW PE), or a pyrolytic carbon (PyC) such as the On-X® carbon made by MCRI. These hard materials obviate the need for a needle stop and prevent passage of a needle inserted into chamber 160 through a rear or side wall of lower base structure 120.

In embodiments of the present invention, retaining ring 105 is provided with a ridge 107 which at least substantially circumscribes a top portion of the retaining ring 105 to permit a health care provider, or even the patient in instances of self-administration of a drug, to percutaneously locate the septum by feeling for the bump(s) of the ridge. This ridge may comprise any shape suitable to positively locate the septum. For example, the ridge could comprise a pair of arcuate sections, a pair of parallel lines, or a plurality of bumps, which would demark outer boundaries of the septum along a portion of the circumference thereof, thereby permitting location of an interior portion of the septum in relation to the ridge sections. Naturally, the ridge could circumscribe septum 110. Retaining ring 105 is also provided with conventional means to facilitate rotation of the retaining ring to permit installation or removal of the threaded retaining ring within a threaded base structure. For example, these means could include a plurality of slots, holes, or edges within which or against which a torque transmitting device can be inserted to rotate the retaining ring 105.

The rate-limiting permeable membrane 150 may comprise a composition such as polyvinyl alcohol, ethylene vinyl acetate, silicone, nylon, polypropylene, polycarbonate, cellulose, cellulose acetate, cellulose esters, polymer composites, Poly(2,6-Dimethylphenylene oxide), or polyether sulfone by diffusion. Diffusion of the drug from the chamber 160 to a target area of the body is controlled by the rate-limiting permeable membrane and by the drug concentration in the chamber. Release rate of the drug from the device is pseudo zero order, though release will begin to slow as the supply of drug in the device is depleted. Importantly, the device of the present invention does not rely on provision of a pressure differential to achieve drug delivery. Rather, release rate is directly proportional to the concentration of the drug in the device and the rate limiting permeable membrane passively regulates drug delivery.

Figure 2:
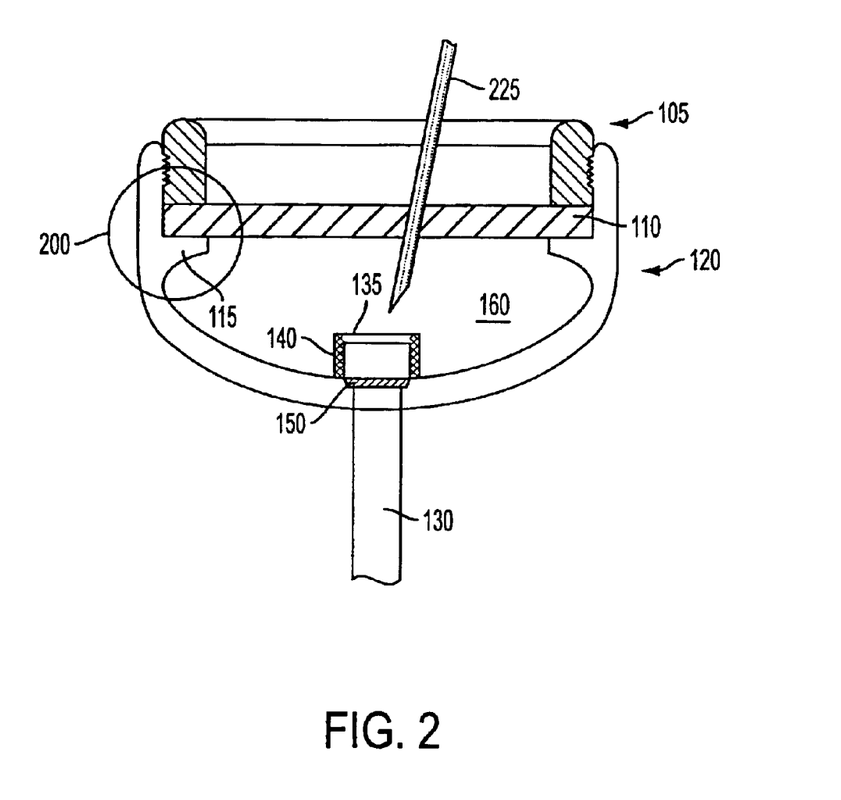
FIG. 2 shows an assembled device in accordance with the present invention.

In embodiments of the present invention, septum 110 is configured to substantially prevent leakage from the first opening and an exterior of the device. Septum 110 may comprise a silicone elastomer material having characteristics which permit repeated, intermittent puncture by a needle 225 as shown in FIG. 2 for injection of drugs from a syringe (not shown). Suitable silicone elastomers include, but are not limited to polyurethane elastomers, polysulfide elastomers, and those manufactured by Dow Corning Corporation of Midland, Mich. (e.g., Dow Corning Q7-4735), Nusil Technology Company's MED-4735, and a composition sold under the trade name "Silastic". Other medically acceptable elastomeric materials may also be employed. Further, septum 110 may include a single material, as described above, or may be a composite material, including a matrix of reinforcing metal fibers (e.g., titanium) or non-metal fibers (e.g., UHMW PE or polypropylene (PP)), for example. Still further, septum 110 may comprise one layer or a plurality of stacked or laminated layers of one or more materials including, for example, a silicon elastomer material. It is generally desired that septum 110 has a thickness between approximately 0.08 and 0.3 inches, but may be thicker or thinner as a whole or in part in accord with the particular application and material. In embodiments of the present invention, a needle smaller than about 20 or 25-gauge is used to facilitate the resealability of the septum 110 following withdrawal of the needle.

To additionally enhance septum 110 resealability, the septum is affixed within the base structure 120 in a slightly compressed state, in a manner known to those skilled in the art, to provide additional external forces to complement the natural resilient action of the elastomer to fill a void created by a needle. To achieve this compressed state, the outer diameter of septum 110 is somewhat larger than the inner diameter of the septum-receiving area 200 within the base portion 120, resulting in an interference fit and providing a fluid-tight seal about a circumference of the septum. Further, retaining ring 105 is provided not only to retain septum 110, but also to compress septum about the circumference thereof when the retaining ring is substantially fully seated. As depicted in FIGS. 1 and 2, for example, retaining ring 105 includes threads 106 on an outer circumference of the ring. Threads 106 may be advantageously arranged to permit adequate compression of the septum 110 by retaining ring 105. For example, the threads may be configured to terminate a predetermined distance D, such as 0.25 inches, above the bottom of the retaining ring so that, upon full seating of the threads, a bottom portion 108 of the retaining ring abuts and compresses septum 110, disposed with an upper surface within the predetermined distance D (e.g., 0.25 inches) from the bottom of the threads, against the septum ledge 115. Thus, retaining ring 105 provides axially compressive forces and radially compressive forces to improve sealing at both the periphery of septum 110 and the interior of the septum.

Figure 4:
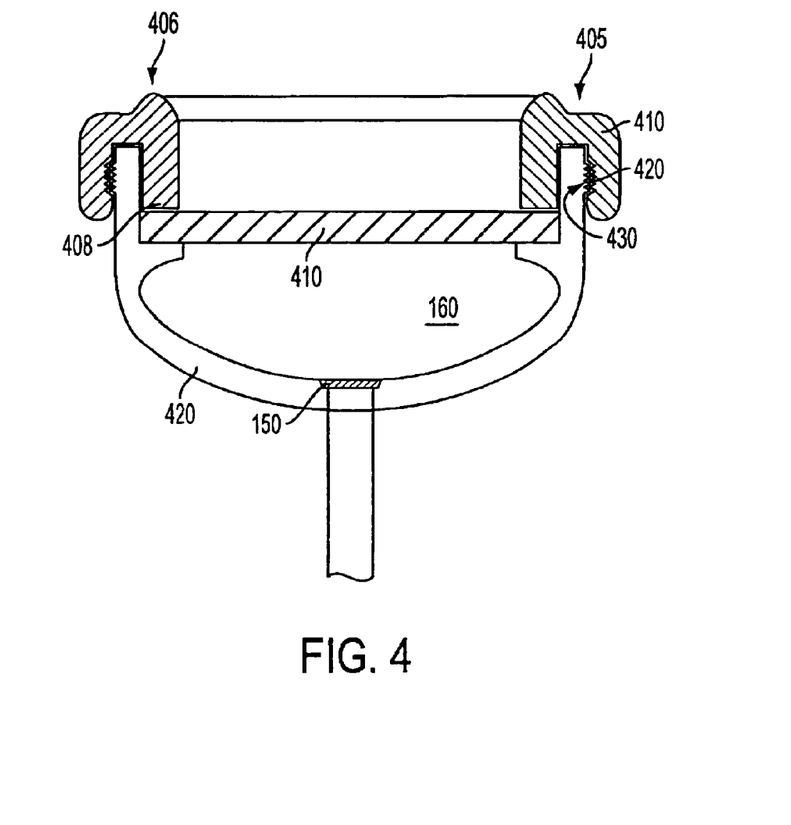
FIG. 4 is a cross-section of a further embodiment of the device of the present invention.

Alternatively, as shown in FIG. 4, the retaining ring 405 may comprise exterior flange portions 410 having threads 420 on an inner circumference thereof engageable with corresponding threads 430 provided on an outer circumference of the base portion 420. A bottom portion 408 of retaining ring 410 abuts and compresses septum 410, as discussed above, to provide axially compressive forces and radially compressive forces to improve sealing at the interior and periphery of septum 410. Ridge 406 is provided to at least substantially circumscribe a top portion of the retaining ring 405 to provide a means permitting a health care provider, or even the patient in instances of self-administration of a medication, to percutaneously locate the septum. This ridge may comprise any shape suitable to positively locate the septum. For example, the ridge could comprise a pair of arcuate sections or a pair of parallel lines, which would demark outer boundaries of the septum along a portion of the circumference thereof, thereby permitting location of an interior portion of the septum in relation to the ridge sections. Naturally, the ridge could entirely circumscribe the septum 410.

Figure 3:
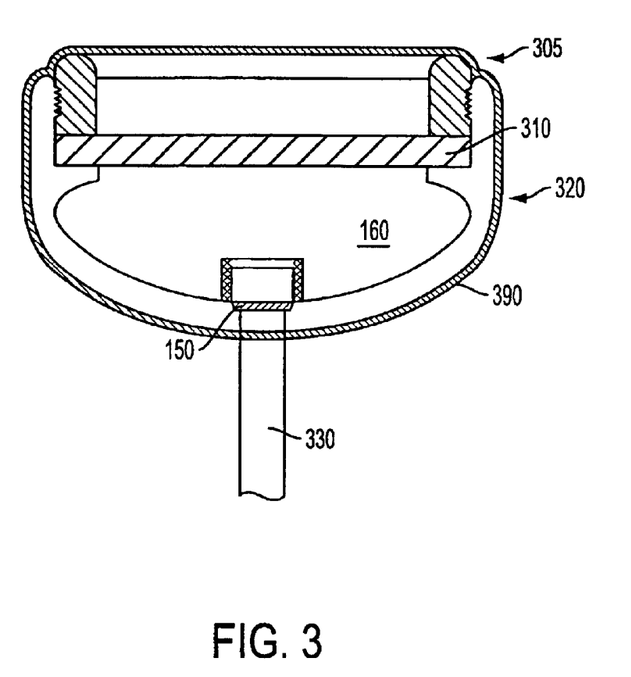
FIG. 3 shows a cross-sectional view of another embodiment of a device in accordance with the present invention.

Still another embodiment is shown in FIG. 3, wherein the device 300 is sealed in a thin elastomeric outer casing 390 to enhance the comfort of the device to a patient, to improve the structural integrity of septum 310 following numerous needle punctures, and to further decrease the potential for leakage at connections such as the base structure 320 and retaining ring 305 connection or the drug delivery tube 330 and base structure connection. This outer casing 390 may be applied in any conventional manner known to those skilled in the art.

The above-described device provides a device which, once implanted, gives continuous access to internal regions of the body without requiring additional needle penetrations into these regions. Instead, a tubular portion of the device, the drug delivery tube 130 and connected tubes, if any, remains in the body and extends to the affected area where it serves as a continuously-available conduit. Thereafter, a syringe or other device need only be placed in fluid communication with this conduit to inject, withdraw or mix fluids in the interior reservoir. The device is also provided with a rate-limiting permeable membrane 150 designed to release the drug to be delivered at a controlled rate.

Figure 5:
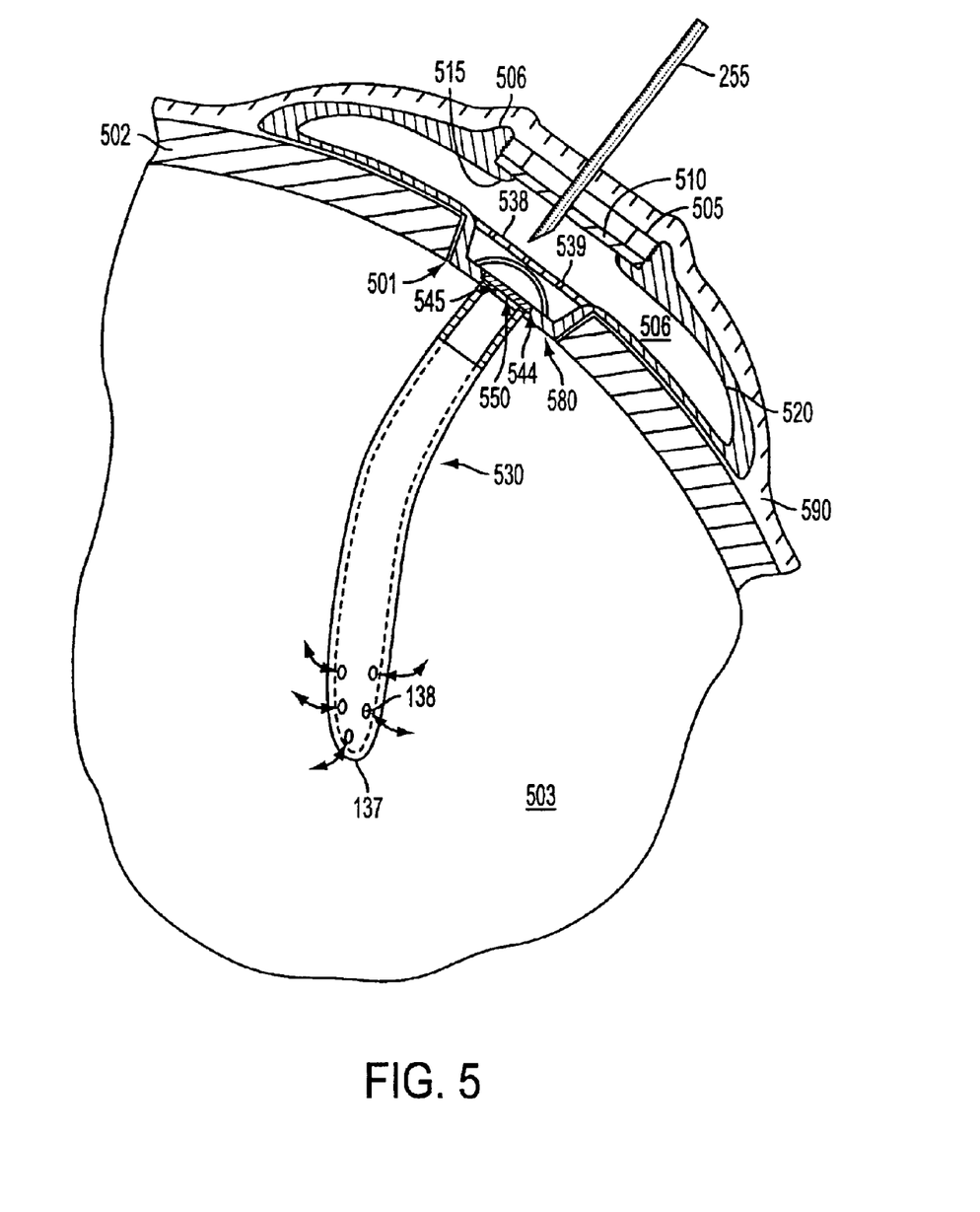
FIG. 5 is a cross-section of yet another device in accordance with the present invention.

In embodiments of the present invention, as depicted in FIG. 5, the device is designed to deliver a drug to a brain tumor at a controlled rate. A controlled delivery rate is particularly important intracranially, wherein even small changes in fluid pressure or volume can cause great distress to the patient. The target region of the brain (tumor) is exposed through a hole 501 drilled in the skull 502, the drug delivery tube 530 positioned to deliver the drug to the appropriate location in the brain 503, and the device secured beneath the skin 590. In this embodiment, the bottom of the base structure 520 comports generally with the curvature of a human skull, having a generally and gently concave shape. As viewed from above, the device 500 has a substantially circular or disk-like shape.

In this application, the device 500 assumes a flattened shape to reduce the profile of the device and hence physical and cosmetic discomfort to the patient. At a center portion of the base structure, a cylindrical section 580 is provided to utilize the periphery of the hole drilled in the skull to position the device and as a lateral support for the implanted device. The reservoir 560 remains outside the skull under the scalp so it can be easily refilled. Diffusion of drug from the reservoir 560 into the tube 530 and hence the brain 503 is controlled by the rate-limiting permeable membrane 550. The rate of delivery into the brain 503 is controlled by the membrane 550 and by the drug concentration in the reservoir 560.

A ridge 506 is integrally provided with the base structure 520 and circumscribes a top portion of the base structure adjacent the retaining ring 505 and permit a health care provider, for example, to percutaneously locate the septum 510 by feeling for the ridge. The rate-limiting permeable membrane 550 is disposed within a recessed area 544 in cylindrical section 580 adjacent the opening 545 to the drug delivery tube 530. A hemispherical filter element 540 is provided to cover the rate-limiting permeable membrane and filter out small foreign substances such as skin, tissue, or septum particles. A needle stop comprising a plate 538 having a plurality of holes 539 smaller in diameter than the smallest usable needle diameter forms, is provided across cylindrical section 580 to form a filter housing. Plate 538 may be affixed to the cylindrical section 580 or base structure 520 in any conventional manner including, but not limited to, bonding, welding, force fitting, threaded connectors, or mating male/female connecting portions.

Alternatively, plate 538 could be integrally formed with base structure 520 and cylindrical section 580 could be affixed to the base structure in one of the above conventional manners to facilitate attachment of any of a plurality of variously sized and configured cylindrical sections, filter elements, and rate-limiting permeable membranes. For example, the cylindrical section 580 could be used as an adapter, allowing a physician or health care provider to use a single base structure 520 with any of a predetermined combination of drug delivery tube sizes, filter sizes, and rate-limiting permeable membranes, the particular combinations selected and/or manufactured for specific procedures and applications.

Septum 510 is affixed within the base structure 520 in a slightly compressed state, as described above, by using a septum 510 having an outer diameter somewhat larger than the inner diameter of the septum-receiving area of the base portion 520, resulting in an interference fit and providing a fluid-tight seal about a circumference of the septum. Retaining ring 505 is screwed into place via the mating threaded portions on the base portion 520 and the retaining ring 505. A bottom portion of retaining ring 505 abuts and compresses septum 510 about the circumference thereof against the septum ledge 515. Thus, retaining ring 105 provides axially compressive forces and radially compressive forces to improve sealing at both the periphery of septum 110 and the interior of the septum.

The use of the device should be evident from the foregoing. The device may be used to control the rate of drug delivery to any internal region of the body. Further, although the above described embodiments illustrate aspects of the invention wherein the device is adapted for drug delivery, the device may also be adapted to withdraw fluid from a targeted region of a patient's body by appropriate regulation of the reservoir pressure and corresponding alteration of the differential pressure across the rate-limiting permeable membrane.

In sum, the invention provides an implantable, refillable reservoir containing a drug solution connected to a delivery tube. The tube is inserted into a specific target region of the body or may be placed in a region such as a blood vessel, to provide systemic distribution of the drug.

Diffusion of the drug from the reservoir into the tube and into the target area of the body is controlled by at least one rate-limiting permeable membrane. The rate of delivery into the target area of the body is controlled by the membrane and by the drug concentration in the reservoir.

In view of the above embodiments, it is to be understood that various other configurations may be employed to connect the retaining ring to the base structure to achieve the compressive securement of a septum within the base structure and to individually, or in combination with the septum, provide a fluid-tight seal. Alternative configurations may include, for example, welding, adhesive bonding, or even snap fit connections between the retaining ring and base structure and the invention is not limited to a specific disclosed construction.

The purpose of the above description and examples is to illustrate some embodiments of the present invention without implying any limitation. It will be apparent to those skilled in the art that various modifications and variations may be made to the device and method of the present invention without departing from the spirit or scope of the invention. All patents and publications cited herein are incorporated by reference in their entireties.

We claim:

1. An implantable, refillable, rate controlled drug delivery device, comprising:
    a base structure having at least a first opening and a second opening, the base structure defining a chamber;
    a septum covering the first opening and configured to substantially prevent leakage from the first opening to an exterior of the device;
    a drug delivery tube comprising a proximal end and a distal end, wherein the proximal end of the tube communicates with the chamber through the second opening, and
    at least one rate-limiting permeable membrane disposed at least partially within said chamber and across a passage between the base structure and said drug delivery tube proximal end, which membrane passively regulates drug delivery.

2. The implantable, refillable, rate controlled drug delivery device according to claim 1, wherein the device comprises two rate-limiting permeable membranes.

3. The implantable, refillable, rate controlled drug delivery device according to claim 1 wherein said at least one rate-limiting permeable membrane is disposed entirely within the chamber.

4. The implantable, refillable, rate controlled drug delivery device according to claim 3, wherein the septum comprises one of a polyvinyl alcohol, ethylene vinyl acetate, silicone, nylon, polypropylene, polycarbonate, cellulose, cellulose acetate, cellulose esters, polymer composites, Poly (2,6-Dimethylphenylene oxide), or polyether sulfone.

5. The implantable, refillable, rate controlled drug delivery device according to claim 1, wherein the chamber contains a drug to be delivered at a controlled rate to a target area of the body.

6. The implantable, refillable, rate controlled drug delivery device according to claim 5, wherein the target area of the body is the brain and the device is configured to deliver the drug thereto.

7. A method of controlling drug delivery to an internal portion of a body comprising administration of a drug to an internal portion of the body through a device according to claim 1 to control delivery of the drug.

8. The implantable, refillable, rate controlled drug delivery device according to claim 1, wherein the septum comprises one of a polyvinyl alcohol, ethylene vinyl acetate, silicone, nylon, polypropylene, polycarbonate, cellulose, cellulose acetate, cellulose esters, polymer composites, Poly (2,6-Dimethylphenylene oxide), or polyether sulfone.

9. The implantable, refillable, rate controlled drug delivery device according to claim 1, wherein the septum comprises at least one of a silicone elastomer, polyurethane elastomer, and polysulfide elastomer.

10. The implantable, refillable, rate controlled drug delivery device comprising:
    a base structure having at least a first opening and a second opening, the base structure defining a chamber;
    a septum covering the first opening and configured to substantially prevent leakage from the first opening to an exterior of the device;
    a drug delivery tube comprising a proximal end and a distal end, wherein the proximal end of the tube communicates with the chamber through the second opening;
    a rate-limiting permeable membrane disposed at least partially within said chamber and across a passage between the base structure and said drug delivery tube proximal end, which membrane passively regulates drug delivery;

a filter housing provided within the chamber adjacent the second opening; and a filter element provided between the rate-limiting permeable membrane and the filter housing.

11. The implantable, refillable, rate controlled drug delivery device according to claim 10, wherein an upper portion of the filter housing comprises a needle stop.

12. The implantable, refillable, rate controlled drug delivery device according to claim 11, wherein the upper portion of the filter housing comprising a needle stop is disposed over the second opening.

13. The implantable, refillable, rate controlled drug delivery device according to claim 12, wherein the upper portion of the filter housing comprising a needle stop comprises a plurality of perforations.

14. The implantable, refillable, rate controlled drug delivery device according to claim 10, further comprising:

a retaining ring for compressively securing the septum in place.

15. The implantable, refillable, rate controlled drug delivery device according to claim 14, wherein the retaining ring and the base structure comprise a biologically compatible metal.

16. The implantable, refillable, rate controlled drug delivery device according to claim 15, wherein the biologically compatible metal comprises one of titanium or stainless steel.

17. The implantable, refillable, rate controlled drug delivery device according to claim 14, wherein the retaining ring and the base structure comprise a substantially rigid non-metallic biologically compatible material.

18. The implantable, refillable, rate controlled drug delivery device according to claim 17, wherein the biologically compatible material comprises one of a Polysulfone, an ultra-high molecular weight polyethylene, organometallic composites, phenolics, unsaturated polyesters, epoxy resins, polycarbonate, polyacetal, nylon, polyimide, and a pyrolytic carbon.

19. A method of controlling the delivery of a drug to an internal portion of a body comprising:

administering a drug to an internal portion of the body through a device according to claim 14 to control the delivery of the drug.

20. An implantable, refillable, rate controlled drug delivery device comprising:

a base structure having at least a first opening and a second opening, the base structure defining a chamber;

a septum covering the first opening and configured to substantially prevent leakage from the first opening to an exterior of the device;

a drug delivery tube comprising a proximal end and a distal end, wherein the proximal end of the tube communicates with the chamber through the second opening;

at least one rate-limiting permeable membrane disposed across a passage between the base structure and the distal end of the drug delivery tube, which membrane passively regulates drug delivery;

a filter housing provided within the chamber adjacent the second opening;

a filter element provided between the rate-limiting permeable membranes and the filter housing, and a depressed region at least partially circumscribing the second opening, wherein an upper portion of the filter housing comprises a needle stop, wherein the upper portion of the filter housing comprising a needle stop is disposed over the second opening, wherein the upper portion of the filter housing comprising a needle stop comprises a plurality of perforations, and wherein the rate-limiting permeable membrane is positioned at least partially within the depressed region.

* * * * *